US010725201B2

(12) United States Patent
Mendez et al.

(10) Patent No.: US 10,725,201 B2
(45) Date of Patent: Jul. 28, 2020

(54) COMPENSATED NEUTRON CORRECTION FOR CONTRIBUTIONS OUTSIDE THE PETROPHYSICAL MODEL

(71) Applicant: Baker Hughes, a GE company, LLC, Houston, TX (US)

(72) Inventors: Freddy Mendez, Kingwood, TX (US); Hao Zhang, The Woodlands, TX (US); John M. Longo, Houston, TX (US)

(73) Assignee: Baker Hughes, a GE Company, LLC, Houston, TX (US)

( * ) Notice: Subject to any disclaimer, the term of this patent is extended or adjusted under 35 U.S.C. 154(b) by 0 days.

(21) Appl. No.: 16/135,100

(22) Filed: Sep. 19, 2018

(65) Prior Publication Data

US 2019/0094409 A1    Mar. 28, 2019

Related U.S. Application Data

(60) Provisional application No. 62/562,175, filed on Sep. 22, 2017.

(51) Int. Cl.
| | |
|---|---|
| *G01V 5/02* | (2006.01) |
| *G01V 5/10* | (2006.01) |
| *G01N 33/24* | (2006.01) |
| *G01V 5/12* | (2006.01) |

(52) U.S. Cl.
CPC .............. *G01V 5/102* (2013.01); *G01N 33/24* (2013.01); *G01V 5/125* (2013.01)

(58) Field of Classification Search
CPC ......... G01V 5/102; G01V 5/125; G01N 33/24
See application file for complete search history.

(56) References Cited

U.S. PATENT DOCUMENTS

| | | | | |
|---|---|---|---|---|
| 4,004,147 A | * | 1/1977 | Allen .................... | G01V 5/107 250/264 |
| 7,408,150 B1 | * | 8/2008 | Flaum ................... | G01V 5/125 250/269.6 |
| 2013/0048849 A1 | * | 2/2013 | Li .......................... | G01V 5/101 250/269.8 |
| 2014/0110575 A1 | * | 4/2014 | Miles ..................... | G01V 5/125 250/256 |

(Continued)

*Primary Examiner* — David P Porta
*Assistant Examiner* — Mamadou Faye
(74) *Attorney, Agent, or Firm* — Mossman Kumar & Tyler PC

(57) ABSTRACT

Estimating a correction factor from logs of compensated thermal neutron porosity measurements, including modeling each measurement of the compensated thermal neutron porosity measurements of the log as resulting from at least: i) a first contribution correlated to an absorbance of a first portion of neutrons produced by irradiation of the volume attributable to interactions in the volume indicative of pore space in the matrix, and ii) a second contribution correlated to an absorbance of a second portion of the neutrons attributable to trace elements of at least one dominant neutron absorber in the formation; iii) a third contribution correlated to an absorbance of a third portion of the neutrons attributable to dry minerals in the matrix other than dominant neutron absorbers; and estimating the second contribution and determining the correction factor from the second contribution; and correcting a compensated thermal neutron porosity measurement using the correction factor.

16 Claims, 12 Drawing Sheets

(56) References Cited

U.S. PATENT DOCUMENTS

| | | | |
|---|---|---|---|
| 2015/0285944 A1* | 10/2015 | Herron | G01N 33/246 |
| | | | 250/269.6 |
| 2017/0227671 A1* | 8/2017 | Zhou | G01V 5/101 |
| 2018/0031732 A1* | 2/2018 | Mosse | G01V 99/005 |

* cited by examiner

Before Excess CN Correction

Improved Porosity Results!

After Excess CN Correction

| ZDNC | CNCLS | DT24 | SIGF |
|---|---|---|---|
| 1.96  2.05 | 5       -5 | 1.40    40 | 55        5 |
| (g.km) [F1] | (pa) [F1] | (km) [F1] | (c1) [F1] |
|  | Exc-CNC |  | Exc-SIG |
|  | 45      -5 |  | 50       0 |
|  | [F1] |  | [F1] |

FIG. 7B

COMPENSATED NEUTRON CORRECTION FOR CONTRIBUTIONS OUTSIDE THE PETROPHYSICAL MODEL

CROSS-REFERENCE TO RELATED APPLICATIONS

This application claims priority from U.S. Provisional Application Ser. No. 62/562,175, filed on Sep. 22, 2017, the entire disclosure of which is incorporated herein by reference in its entirety.

FIELD OF THE DISCLOSURE

In one aspect, this disclosure generally relates to methods, devices and systems for estimating at least one parameter of interest relating to a volume using nuclear radiation based measurements.

BACKGROUND OF THE DISCLOSURE

Well logging systems have been utilized in hydrocarbon exploration for many years. Such systems provide data for use by geologists and petroleum engineers in making many determinations pertinent to hydrocarbon exploration. In particular, these systems provide data for subsurface structural mapping, defining the lithology of subsurface formations, identifying hydrocarbon-productive zones, and interpreting reservoir characteristics and contents.

One class of systems seeks to measure incidence of nuclear particles on the well logging tool from the formation for purposes well known in the art. These systems take various forms, including those measuring natural gamma rays from the formation. Still other systems measure gamma rays in the formation caused by bursts of neutrons into the formation by a pulsed neutron source carried by the tool. A rigid or non-rigid conveyance device is often used to convey the nuclear radiation source, often as part of a tool or a set of tools, and the carrier may also provide communication channels for sending information up to the surface.

SUMMARY OF THE DISCLOSURE

In aspects, the present disclosure is related to methods and apparatuses for estimating at least one parameter of interest of a volume of interest of an earth formation using nuclear radiation based measurements.

Aspects may include methods, systems, and devices for estimating at least one property of a volume of interest of an earth formation from a compensated thermal neutron porosity measurement. The volume of interest surrounds a borehole intersecting the earth formation, wherein the formation contains trace elements of at least one dominant thermal neutron absorber causing non-hydrogen thermal neutron absorption. Methods may include estimating a correction factor by processing a log of compensated thermal neutron porosity measurements taken in a fluid-saturated rock matrix. Processing may include modeling each measurement of the compensated thermal neutron porosity measurements of the log as resulting from at least: i) a first contribution correlated to an absorbance of a first portion of neutrons produced by irradiation of the volume attributable to interactions in the volume indicative of pore space in the matrix, ii) a second contribution correlated to an absorbance of a second portion of the neutrons produced by the irradiation of the volume attributable to trace elements of at least one dominant neutron absorber in the formation, iii) a third contribution correlated to an absorbance of a third portion of the neutrons produced by the irradiation of the volume attributable to dry minerals in the matrix other than dominant neutron absorbers; and estimating the second contribution and determining the correction factor from the second contribution; and correcting a compensated thermal neutron porosity measurement using the correction factor to produce a corrected compensated thermal neutron porosity measurement. The second contribution may be modeled as excess porosity.

The log of compensated thermal neutron porosity measurements may comprise a varying location-dependent compensated thermal neutron porosity measurement. The interactions in the volume indicative of pore space in the matrix predominantly may comprise neutron absorption by hydrogen. The parameter of interest may be the corrected compensated thermal neutron porosity.

Methods may include estimating the correction factor by jointly processing the log of compensated thermal neutron porosity measurements in combination with a second log of a location-dependent non-porosity measurement. Processing may include modeling the measurements of the second log as resulting from at least: i) a first contribution correlated to an absorbance of a first portion of neutrons produced by irradiation of the volume attributable to interactions in the volume indicative of pore space in the matrix, ii) a second contribution correlated to an absorbance of a second portion of the neutrons produced by the irradiation of the volume attributable to trace elements of at least one dominant neutron absorber in the formation, iii) a third contribution correlated to an absorbance of a third portion of the neutrons produced by the irradiation of the volume attributable to dry minerals in the matrix other than dominant neutron absorbers; and estimating the second contribution and determining the correction factor from the second contribution. The second log may be a log of thermal neutron capture cross section measurements.

Methods may include estimating the second contribution of the first log by performing an inversion using the results of the first log and the second log. Methods may include constraining the inversion with the constraint that each second contribution of the first log is a function of the second contribution of a corresponding measurement of the second log, or constraining the inversion with the constraint that each second contribution of the first log is a function of both the corresponding measurement and the second contribution of the corresponding measurement of the second log. Methods may include estimating a correlation function defining a second contribution of a measurement of the first log as a function of at least one of: i) a corresponding measurement of the second log, and ii) a second contribution of the corresponding measurement of the second log. Performing the inversion may comprise determining a best fit using a least square error. Methods may include determining the first contribution and the third contribution from a priori information, and calculating the second contribution from the first contribution, the third contribution, and the corresponding measurement. Methods may include determining the first contribution as a sum of respective contributions from volume fractions of a plurality of candidate minerals.

Methods may include generating a simulated theoretical clean compensated neutron response and a simulated theoretical clean compensated neutron response; comparing the simulated theoretical clean compensated neutron response with the log of compensated thermal neutron porosity measurements to estimate the second contribution of the log of compensated thermal neutron porosity measurements; and comparing the simulated theoretical clean compensated neutron response with the measurements of the second log to estimate the second contribution of the second log.

Methods may include conducting further operations in the formation in dependence upon the calibrated radiation measurement. Further operations may include at least one of: i) geosteering; ii) drilling at least one borehole in the formation; iii) performing measurements on the formation; iv) estimating at least one parameter of interest of the formation; v) installing equipment in a borehole in the formation; vi) evaluating the formation; vii) optimizing development in the formation; viii) optimizing development in a formation related to the formation; ix) optimizing exploration in the formation; x) optimizing exploration in a formation related to the formation; xi) producing at least one hydrocarbon from the formation.

Apparatus embodiments may include a carrier having a tool disposed thereon and configured for conveyance in a borehole. The tool may be configured to make radiation-based measurements including a compensated thermal neutron porosity measurements. The tool may include at least one information processing device configured for estimating a correction factor by processing compensated thermal neutron porosity measurements taken in a fluid-saturated rock matrix. Processing may include modeling each measurement of the compensated thermal neutron porosity measurements of the log as resulting from at least: i) a first contribution correlated to an absorbance of a first portion of neutrons produced by irradiation of the volume attributable to interactions in the volume indicative of pore space in the matrix, and ii) a second contribution correlated to an absorbance of a second portion of the neutrons produced by the irradiation of the volume attributable to trace elements of at least one dominant neutron absorber in the formation, iii) a third contribution correlated to an absorbance of a third portion of the neutrons produced by the irradiation of the volume attributable to dry minerals in the matrix other than dominant neutron absorbers; estimating the second contribution and determining the correction factor from the second contribution; and correcting a compensated thermal neutron porosity measurement using the correction factor to produce a corrected compensated thermal neutron porosity measurement.

Embodiments may employ a pulsed neutron source. The information processing device may comprise at least one processor; and a memory storage medium accessible to the at least one processor. Methods as described above implicitly utilize at least one processor. Apparatus embodiments may include, in addition to specialized borehole measurement equipment and conveyance apparatus, at least one processor and a computer memory accessible to the at least one processor having instructions thereon that, when executed, causes the at least one processor to perform methods described above. Some embodiments include a non-transitory computer-readable medium product accessible to the processor and having instructions thereon that, when executed, causes the at least one processor to perform methods described above.

Examples of the more important features of the disclosure have been summarized rather broadly in order that the detailed description thereof that follows may be better understood and in order that the contributions they represent to the art may be appreciated.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals, wherein:

FIGS. 7A & 7B show processing results before and after applying excess-neutron correction for a shale gas well, respectively;

DETAILED DESCRIPTION

In aspects, this disclosure relates to estimating at least one parameter of interest of a volume of interest by detecting radiation incident on the tool and, more particularly, to properly correcting radiation measurements. In some aspects, this disclosure relates to estimating a parameter of interest (related to a volume of interest) from radiation information. The volume may include an earth formation, such as, for example, an earth formation surrounding a borehole. The parameter of interest may be a physical characteristic of the volume, such as, for example, density.

In these nuclear well logging systems, reliance is made upon the physical phenomenon that the energies of neutrons returning to the tool are indicative of the presence of certain elements within the formation. In other words, formation elements will react in predictable ways, for example, when neutrons collide with the formation elements. Particularly, the interaction of thermal neutrons with hydrogen is indicative of several parameters of interest of the formation.

Prior art methods exist for determining attributes of a formation from logging results. See, for example, U.S. Pat. No. 3,321,625 to Wahl, U.S. Pat. No. 3,566,177 to Larson, U.S. Pat. No. 4,390,783, to Grau, U.S. Pat. No. 4,570,067 issued to Gadeken, U.S. Pat. No. 4,810,459 to Fontenot, U.S. Pat. No. 4,910,397 to Mills, Jr. et al., U.S. Pat. No. 5,684,299 to DasGupta, U.S. Pat. No. 5,789,752 to Mickael et al, and U.S. Pat. No. 9,341,737 to Inanc et al., all incorporated herein by reference in their entirety.

Each of the embodiments herein may be used in a variety of settings in both drilling and non-drilling environments. In some implementations, the disclosed embodiments may be used in connection with LWD or MWD tools as part of a drilling system, while in other implementations embodiments may be incorporated into other types of well tools, such as wireline or slickline systems.

Figure 1A:
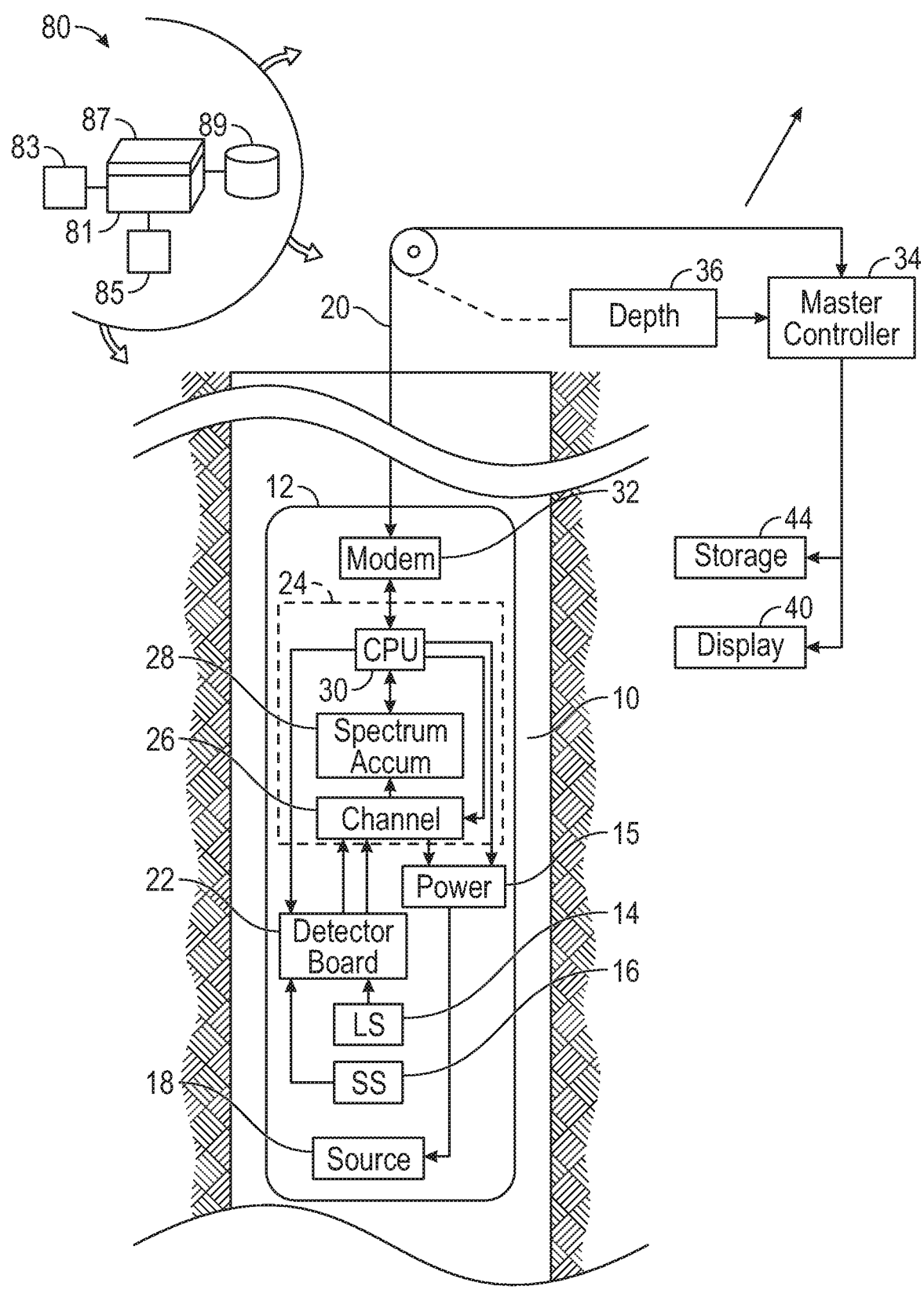
FIG. 1A illustrates a nuclear well logging system in accordance with embodiments of the present disclosure.

Referring now to the drawings in more detail, and particularly to FIG. 1A, there is illustrated a nuclear well logging configuration in accordance with the present invention. Well 10 penetrates the earth's surface and may or may not be cased depending upon the particular well being investigated. Disposed within well 10 is subsurface well logging instrument 12. The system diagramed in FIG. 1A is a microprocessor-based nuclear well logging system using multi-channel scale analysis for determining the timing distributions of the detected gamma rays. Well logging instrument 12 may include at least one detector 14, 16 and a pulsed neutron source 18. The at least one detector may be configured as a long-spaced (LS) detector 14 and a short-spaced (SS) detector 16. In an exemplary embodiment, LS and SS detectors 14 and 16 may be comprised of LYSO ($Lu^1$-$xYxSi^2O^5$) crystals coupled to photomultiplier tubes. In other examples, crystals of CsI(Na), NaI(Tl), BGO or GSO may be used, or joined fiber materials may be employed which are made up of fibers comprising crystalline scintillation materials (e.g., LuAG and YAG), amorphous glass, nanostructured glass ceramics, and so on.

To protect the detector systems from the high temperatures encountered in boreholes, the detector system may be mounted in a Dewar-type flask. Also, in an exemplary embodiment, source 18 comprises a pulsed neutron source using a D-T reaction wherein deuterium ions are accelerated into a tritium target, thereby generating neutrons having an energy of approximately 14 MeV. The filament current and accelerator voltage are supplied to source 18 through power supply 15. Cable 20 suspends instrument 12 in well 10 and contains the required conductors for electrically connecting instrument 12 with the surface apparatus.

The outputs from LS and SS detectors 14 and 16 are coupled to detector board 22, which amplifies these outputs and compares them to an adjustable discriminator level for passage to channel generator 26. Channel generator 26 converts the output pulse heights to digital values, which are accumulated into pulse height spectra, in which the pulses are sorted according to their amplitudes into a discrete array of bins. The bins uniformly divide the entire amplitude range. These pulse height spectra are accumulated in registers in the spectrum accumulator 28, the spectra being sorted according to their type: inelastic, capture, or background. After a pulse height spectrum has been accumulated, CPU 30 controls the transfer of the accumulated data to the modem 32, which is coupled to cable 20 for transmission of the data over a communication link to the surface apparatus. To be explained later are further functions of CPU 30 in communicating control commands which define certain operational parameters of instrument 12 including the discriminator levels of detector board 22, and the filament current and accelerator voltage supplied to source 18 by power supply 15.

The surface apparatus includes master controller 34 coupled to cable 20 for recovery of data from instrument 12 and for transmitting command signals to instrument 12. There is also associated with the surface apparatus depth controller 36 which provides signals to master controller 34 indicating the movement of instrument 12 within well 10. An input terminal may be coupled to master controller or processor 34 to allow the system operator to provide selected input into master controller 34 for the logging operation to be performed by the system. Display unit 40, and storage unit 44 coupled to the master controller 34 may be provided. The data may also be sent by a link to a remote location. Processing may be done either by the surface processor, at the remote site, or by a downhole processor.

Master controller 34 initially transmits system operation programs and command signals to be implemented by CPU 30, such programs and signals being related to the particular well logging operation. Instrument 12 is then caused to traverse well 10 in a conventional manner, with source 18 being pulsed in response to synchronization signals from channel generator 26. Typically, source 18 is pulsed at a rate of 10,000 bursts/second (10 kHz). This, in turn, causes a burst of high-energy neutrons on the order of 14 MeV to be introduced into the surrounding formation to be investigated. In a manner previously described, this population of high energy neutrons introduced into the formation will cause the generation of gamma rays within the formation which at various times will impinge on LS and SS detectors 14 and 16. As each gamma ray thus impinges upon the crystal-photomultiplier tube arrangement of the detectors, a voltage pulse having an amplitude functionally related to the energy of the particular gamma ray is delivered to detector board 22. Detector board 22 amplifies each pulse and compares them to an adjustable discriminator level, typically set at a value corresponding to approximately 100 keV. If such pulse has an amplitude corresponding to an energy of at least approximately 100 keV, the voltage pulse is transformed into a digital signal and passed to channel generator 26 of MCS section 24.

Figure 1B:
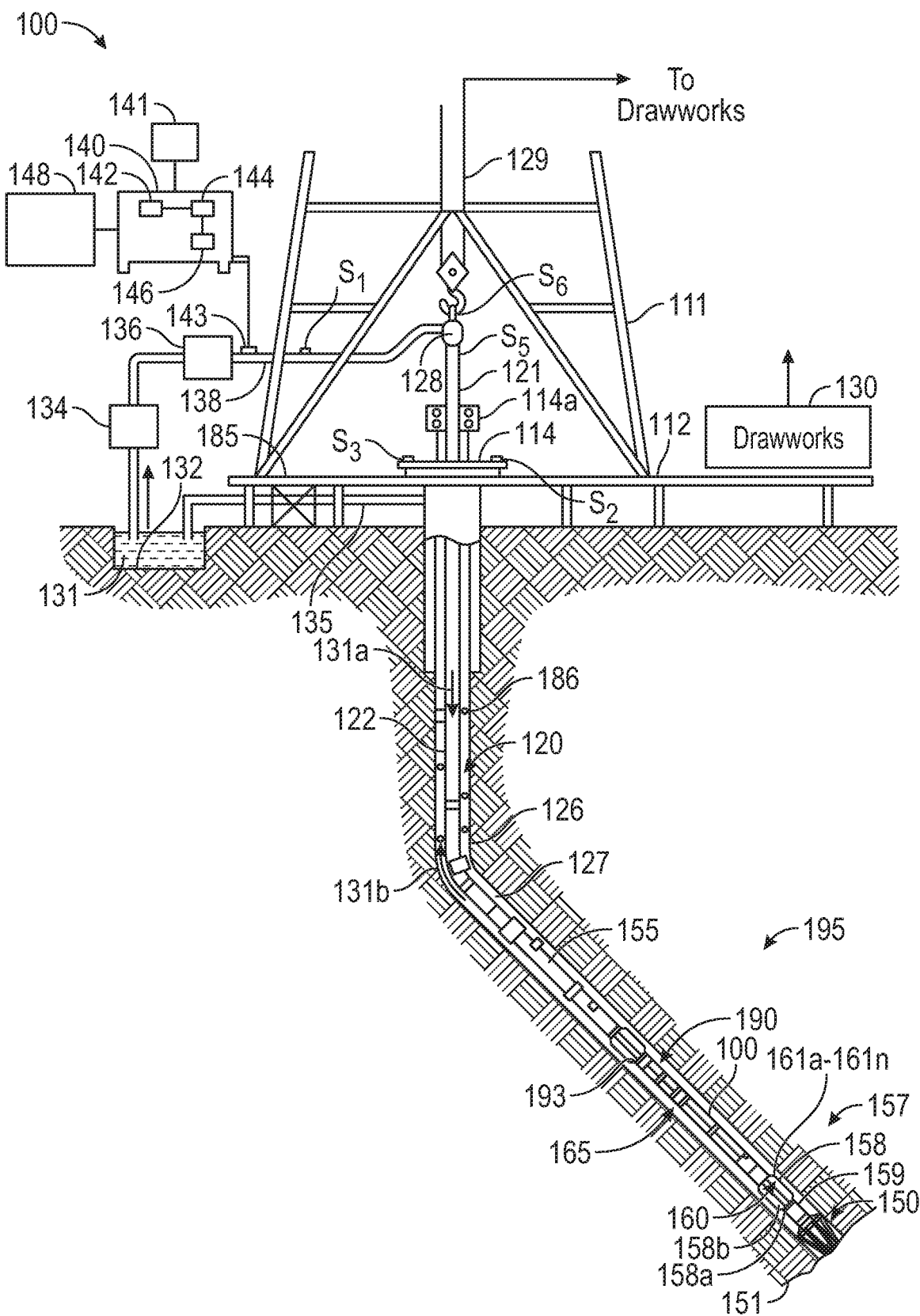
FIG. 1B is a schematic diagram of an exemplary drilling system that includes a drill string having a drilling assembly attached to its distal end in accordance with embodiments of the present disclosure.

FIG. 1B is a schematic diagram of an exemplary drilling system 100 that includes a drill string having a drilling assembly attached to its bottom end that includes a steering unit according to one embodiment of the disclosure. FIG. 1B shows a drill string 120 that includes a drilling assembly or bottomhole assembly (BHA) 190 conveyed in a borehole 126. The drilling system 100 includes a conventional derrick 111 erected on a platform or floor 112 which supports a rotary table 114 that is rotated by a prime mover, such as an electric motor (not shown), at a desired rotational speed. A tubing (such as jointed drill pipe 122), having the drilling assembly 190, attached at its bottom end extends from the surface to the bottom 151 of the borehole 126. A drill bit 150, attached to drilling assembly 190, disintegrates the geological formations when it is rotated to drill the borehole 126. The drill string 120 is coupled to a drawworks 130 via a Kelly joint 121, swivel 128 and line 129 through a pulley. Drawworks 130 is operated to control the weight on bit ("WOB"). The drill string 120 may be rotated by a top drive (not shown) instead of by the prime mover and the rotary table 114. Alternatively, a coiled-tubing may be used as the tubing 122. A tubing injector 114a may be used to convey the coiled-tubing having the drilling assembly attached to its bottom end. The operations of the drawworks 130 and the tubing injector 114a are known in the art and are thus not described in detail herein.

A suitable drilling fluid 131 (also referred to as the "mud") from a source 132 thereof, such as a mud pit, is circulated under pressure through the drill string 120 by a mud pump 134. The drilling fluid 131 passes from the mud pump 134 into the drill string 120 via a desurger 136 and the fluid line 138. The drilling fluid 131a from the drilling tubular discharges at the borehole bottom 151 through openings in the drill bit 150. The returning drilling fluid 131b circulates uphole through the annular space 127 between the drill string 120 and the borehole 126 and returns to the mud pit 132 via a return line 135 and drill cutting screen 185 that removes the drill cuttings 186 from the returning drilling fluid 131b. A sensor $S_1$ in line 138 provides information about the fluid flow rate. A surface torque sensor $S_2$ and a sensor $S_3$ associated with the drill string 120 respectively provide information about the torque and the rotational speed of the drill string 120. Tubing injection speed is determined from the sensor $S_5$, while the sensor $S_6$ provides the hook load of the drill string 120.

In some applications, the drill bit 150 is rotated by only rotating the drill pipe 122. However, in many other applications, a downhole motor 155 (mud motor) disposed in the drilling assembly 190 also rotates the drill bit 150. The rate of penetration (ROP) for a given BHA largely depends on the WOB or the thrust force on the drill bit 150 and its rotational speed.

The mud motor 155 is coupled to the drill bit 150 via a drive shaft disposed in a bearing assembly 157. The mud motor 155 rotates the drill bit 150 when the drilling fluid 131 passes through the mud motor 155 under pressure. The bearing assembly 157, in one aspect, supports the radial and axial forces of the drill bit 150, the down-thrust of the mud motor 155 and the reactive upward loading from the applied weight-on-bit.

A surface control unit or controller 140 receives signals from the downhole sensors and devices via a sensor 143 placed in the fluid line 138 and signals from sensors $S_1$-$S_6$ and other sensors used in the system 100 and processes such signals according to programmed instructions provided to the surface control unit 140. The surface control unit 140 displays desired drilling parameters and other information on a display/monitor 141 that is utilized by an operator to control the drilling operations. The surface control unit 140 may be a computer-based unit that may include a processor 142 (such as a microprocessor), a storage device 144, such as a solid-state memory, tape or hard disc, and one or more computer programs 146 in the storage device 144 that are accessible to the processor 142 for executing instructions contained in such programs. The surface control unit 140 may further communicate with a remote control unit 148. The surface control unit 140 may process data relating to the drilling operations, data from the sensors and devices on the surface, data received from downhole, and may control one or more operations of the downhole and surface devices. The data may be transmitted in analog or digital form.

The BHA 190 may also contain formation evaluation sensors or devices (also referred to as measurement-while-drilling ("MWD") or logging-while-drilling ("LWD") sensors) determining resistivity, density, porosity, permeability, acoustic properties, nuclear-magnetic resonance properties, formation pressures, properties or characteristics of the fluids downhole and other desired properties of the formation 195 surrounding the BHA 190. Such sensors are generally known in the art and for convenience are generally denoted herein by numeral 165. The BHA 190 may further include a variety of other sensors and devices 159 for determining one or more properties of the BHA 190 (such as vibration, bending moment, acceleration, oscillations, whirl, stick-slip, etc.) and drilling operating parameters, such as weight-on-bit, fluid flow rate, pressure, temperature, rate of penetration, azimuth, tool face, drill bit rotation, etc.) For convenience, all such sensors are denoted by numeral 159.

The BHA 190 may include a steering apparatus or tool 158 for steering the drill bit 150 along a desired drilling path. In one aspect, the steering apparatus may include a steering unit 160, having a number of force application members 161a-161n, wherein the steering unit is at partially integrated into the drilling motor. In another embodiment, steering apparatus may include a steering unit 158 having a bent sub and a first steering device 158a to orient the bent sub in the wellbore and the second steering device 158b to maintain the bent sub along a selected drilling direction.

The drilling system 100 may include sensors, circuitry and processing software and algorithms for providing information about desired dynamic drilling parameters relating to the BHA, drill string, the drill bit and downhole equipment such as a drilling motor, steering unit, thrusters, etc. Exemplary sensors include, but are not limited to drill bit sensors, an RPM sensor, a weight on bit sensor, sensors for measuring mud motor parameters (e.g., mud motor stator temperature, differential pressure across a mud motor, and fluid flow rate through a mud motor), and sensors for measuring acceleration, vibration, whirl, radial displacement, stick-slip, torque, shock, vibration, strain, stress, bending moment, bit bounce, axial thrust, friction, backward rotation, BHA buckling, and radial thrust. Sensors distributed along the drill string can measure physical quantities such as drill string acceleration and strain, internal pressures in the drill string bore, external pressure in the annulus, vibration, temperature, electrical and magnetic field intensities inside the drill string, bore of the drill string, etc. Suitable systems for making dynamic downhole measurements include COPILOT, a downhole measurement system, manufactured by Baker Hughes, a GE company, LLC.

The drilling system 100 can include one or more downhole processors at a suitable location such as 193 on the BHA 190. The processor(s) can be a microprocessor that uses a computer program implemented on a suitable non-transitory computer-readable medium that enables the processor to perform the control and processing. The non-transitory computer-readable medium may include one or more ROMs, EPROMs, EAROMs, EEPROMs, Flash Memories, RAMs, Hard Drives and/or Optical disks. Other equipment such as power and data buses, power supplies, and the like will be apparent to one skilled in the art. In one embodiment, the MWD system utilizes mud pulse telemetry to communicate data from a downhole location to the surface while drilling operations take place. The surface processor 142 can process the surface measured data, along with the data transmitted from the downhole processor, to evaluate formation lithology. While a drill string 120 is shown as a conveyance system for sensors 165, it should be understood that embodiments of the present disclosure may be used in connection with tools conveyed via rigid (e.g. jointed tubular or coiled tubing) as well as non-rigid (e. g. wireline, slickline, e-line, etc.) conveyance systems. The drilling system 100 may include a bottomhole assembly and/or sensors and equipment for implementation of embodiments of the present disclosure on either a drill string or a wireline. A point of novelty of the system illustrated in FIG. 1 is that the surface processor 142 and/or the downhole processor 193 are configured to perform certain methods (discussed below) that are not in prior art.

Figure 2:
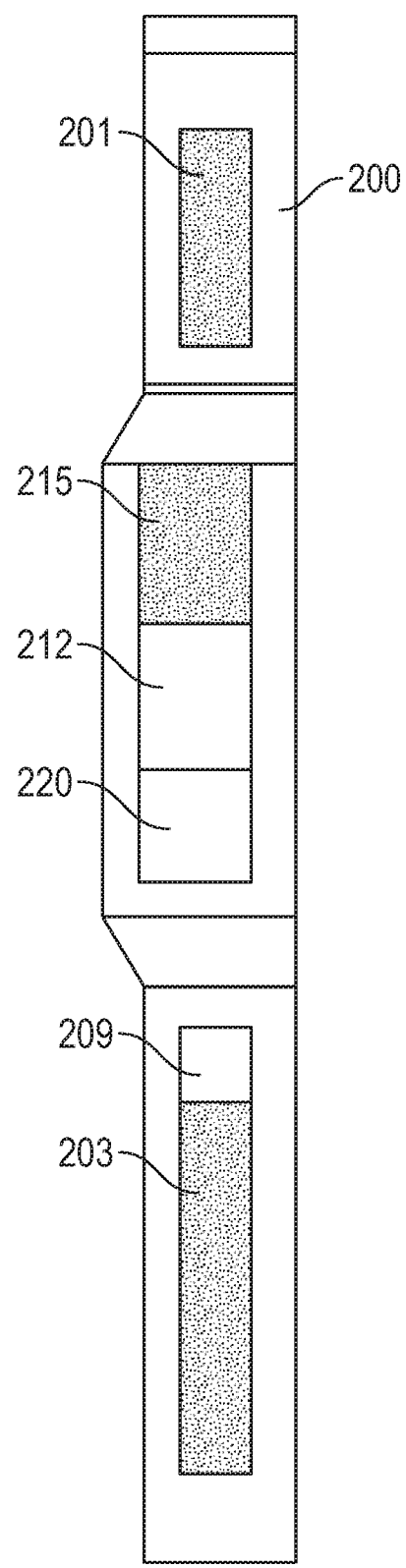
FIG. 2 illustrates a schematic diagram of an instrument suitable for use in accordance with embodiments of the present disclosure.

FIG. 2 illustrates a schematic diagram of an instrument suitable for use with the present invention. The Formation Lithology Explorer™ ('FLEX') is a wireline instrument designed to provide formation mineralogical information, shale identification, and clay typing. The enhanced mineralogical data obtained from the FLEX also enables enhanced porosity measurements. The present invention is usable in open-hole wireline logging systems. In a typical embodiment, the present invention uses the ECLIPS™ acquisition system of Baker Hughes Incorporated. Alternatively, the present invention can be used, for example, with the FOCUS system of Baker Hughes, Incorporated. Also, under most conditions, the FLEX™ is run in combination with Gamma Ray/Spectralog, Neutron, and Density nuclear tools in addition to tools such as resistivity, acoustics, NMR and others. The FLEX utilizes an axial pulsed neutron generator of the same type as that used in the reservoir performance monitor instruments. Thus, there are no special storage or transportation requirements except those of a regulatory nature associated with pulsed neutron generators. The logging speed is dependent upon the environment. A typical logging speed is in the range of 15-60 feet/minute.

The FLEX™ measurement device of FIG. 2 employs the principle of neutron-induced gamma ray spectroscopy. FLEX™ component parts may be encapsulated within wireline device casing 200. The neutron source of the present invention is typically a pulsed neutron source. The use of a pulsed neutron source is advantageous over the use of a chemical neutron source due to its ability to generate inelastic gamma rays over a wider range of energies. It also allows a spectrum of capture gamma rays to be generated which is free from inelastic gamma ray contamination, which can also be corrected for background activation gamma rays. Neutron source 209 discharges high-energy bursts of neutrons into the surrounding formation. The electronic pulsed neutron generator is typically operated at a rate of approximately 10,000 Hz, so that each burst takes place within a 100 microsecond window. Gamma rays produced via interaction of the discharged neutrons and the formation are detected at the scintillation detector 212 attached to acquisition and telemetry electronics 215. Power supply 201 enables the FLEX device. Electronics 203 enables the neutron source. A shield 220 attenuates the neutron flux propagating directly from the source to the detector as well as attenuating gamma rays generated within the shield.

Figure 3:
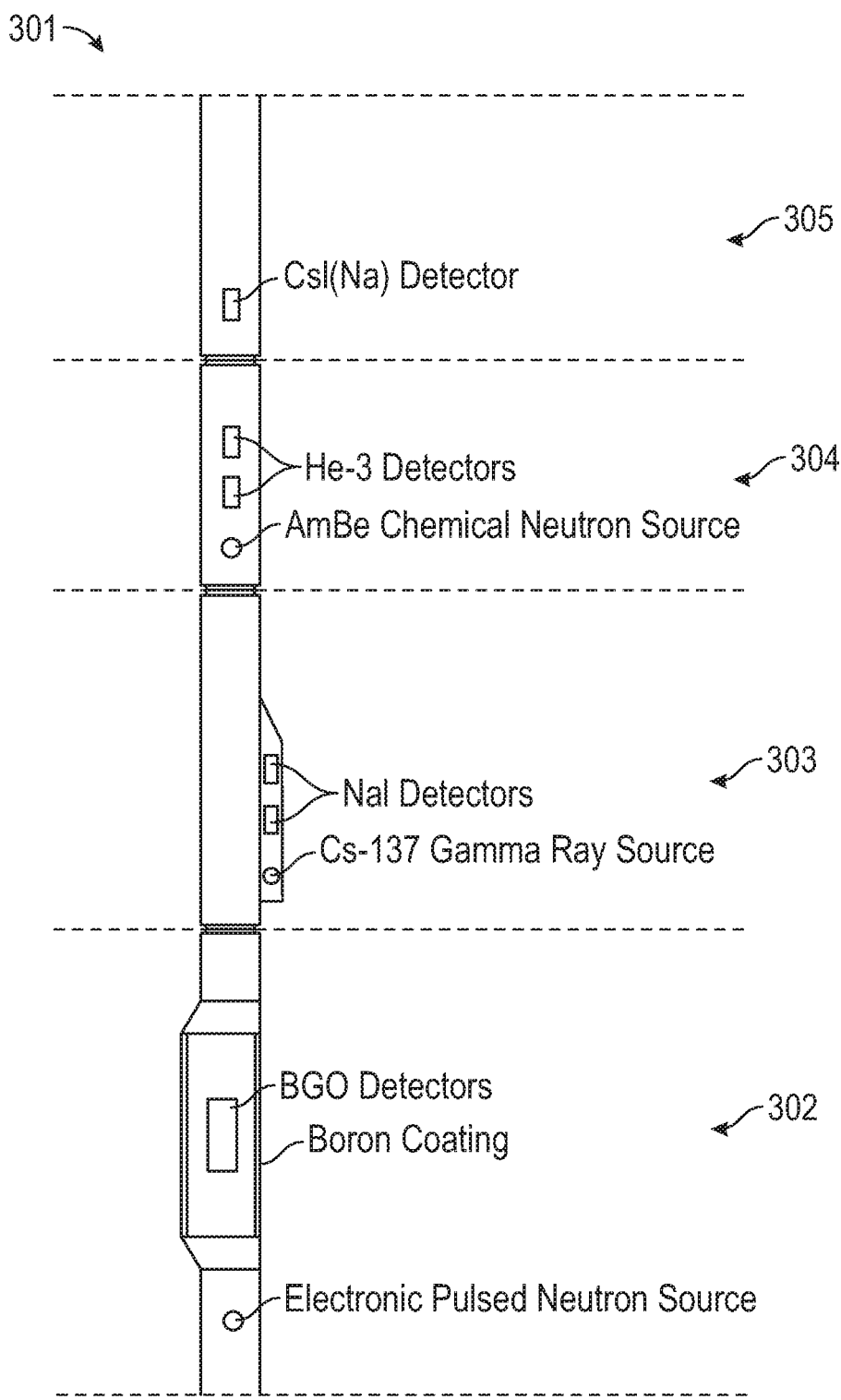
FIG. 3 illustrates exemplary components of a logging string of the present disclosure.

FIG. 3 illustrates exemplary components of a logging string of the present disclosure. The instruments on the logging string 301 may include: a pulsed neutron tool 302 of the kind described above; a density tool 303, a natural gamma ray tool 305; and a neutron porosity tool 304. The natural gamma ray tool 305 provides data that is processed to give elemental information on Potassium (K), Thorium (Th) and Uranium (U). The pulsed neutron measurements may be analyzed to give an elemental analysis of other elements using the method discussed in U.S. Pat. No. 7,205,535 to Madigan et al., having the same assignee as the present disclosure and the contents of which are incorporated herein by reference, wherein an elemental analysis of the pulsed neutron measurements is carried out. The ensemble of tools used may be referred to as a downhole assembly.

While a wireline is shown as a conveyance system for the nuclear detection module, it should be understood that embodiments of the present disclosure may be used in connection with tools conveyed via rigid (e.g. jointed tubular or coiled tubing) as well as non-rigid (e. g. wireline, slickline, e-line, etc.) conveyance systems.

Compensated Pulsed Neutron

Well logging systems for measuring neutron absorption in a formation may use a pulsed neutron source providing bursts of very fast, high-energy neutrons. Pulsing the neutron source permits the measurement of parameters such as, for example, the macroscopic thermal neutron absorption capture cross-section $\Sigma$ of a formation. The capture cross-section of a reservoir rock may be indicative of the quantity and type of hydrocarbons contained in the pore spaces, as well as being sensitive to the elements of the rock matrix. The measurement of neutron population decay rate may be made cyclically. The neutron source is pulsed for up to 40 microseconds to create a neutron population. Neutrons leaving the pulsed source interact with the surrounding environment and are slowed down. In a well logging environment, collisions between the neutrons and the surrounding fluid and formation atoms act to slow these neutrons.

Neutron porosity well logging instruments are responsive primarily to the volumetric concentration of hydrogen nuclei within earth formations. The volumetric concentration of hydrogen nuclei is related to the fractional volume of pore space (referred to as the "porosity") of the earth formation. Typically, fluids in the pore space predominantly comprise water, hydrocarbons, or a combination of these. Both water and hydrocarbons include hydrogen. Indications of high volumetric concentrations of hydrogen, therefore, typically correspond to high fractional volumes of fluid-filled pore space ("porosity").

Compensated thermal neutron instruments have a plurality of detectors sensitive to neutrons. The detectors are positioned at spaced apart locations from a source of high energy neutrons, which may be a chemical source or a neutron generator. In operation, the high energy neutrons emitted from the steady-state source travel into the formation where they gradually lose energy (e.g., from collision with hydrogen nuclei). The lower energy neutrons are detected by detectors on the tool spaced at respective distances from the source. These methods should not be confused with seminal methods directed to epithermal neutron measurement indicative of the slowing process, which suffer from large environmental effects, or with techniques relating to capture gamma rays, which are sensitive to formation density effects on the diffusion of the gamma rays from the formation to the detector.

Compensated thermal neutron instruments are typically configured so that the numbers or rate of neutrons detected (e.g., counts or count rates) by each of the detectors are processed according to a relation between the count rates, such as, for example, scaled into a ratio of count rates. A common practice is to scale the count rate of the detector closer to the source (the "near" detector) with respect to the count rate of the more spaced apart ("far") detector. The count rate ratio can be further scaled, by methods well known in the art, into a measurement corresponding to formation porosity. This measurement may be further modified or adjusted to compensate for environmental conditions. Comparative measurement values of this type, whether environmentally corrected or raw, are referred to herein as "compensated thermal neutron porosity."

Neutron porosity devices have been used in formation evaluation for more than seventy years. The most popular method for modern neutron logging tools uses dual detectors which can effectively provide high count rate and borehole compensation. In compensated neutron porosity logging, a data acquisition system generates a compensated neutron porosity measurement representative of the porosity of the formation and derived from detection of neutrons at a plurality of detectors. The calculated thermal neutron density ('TND'), directly related to count rate, may be plotted as a function of distance from the neutron source in a porous media. See Gilchrist and Koudelka (1994).

Figure 4:
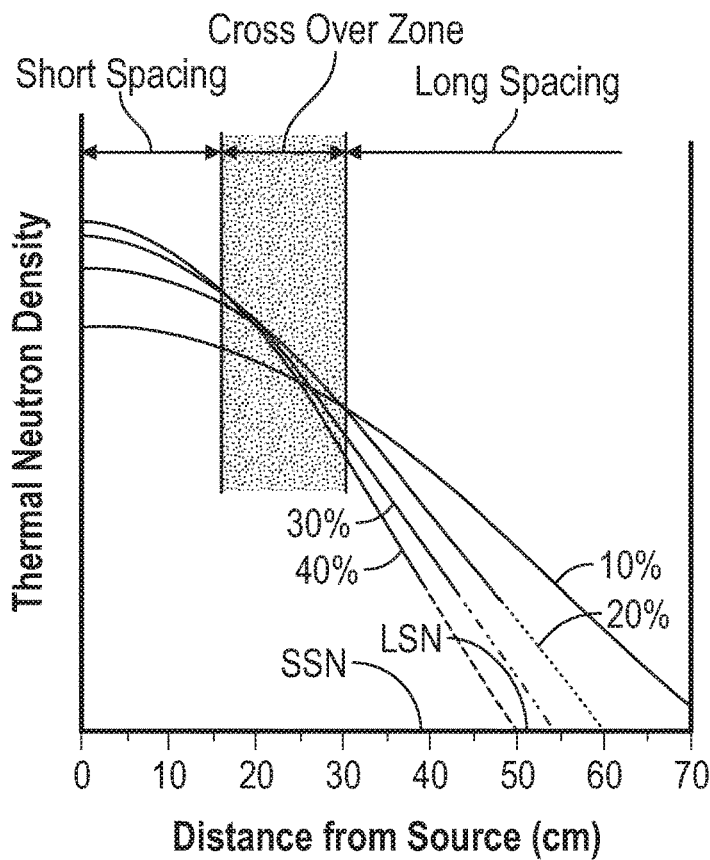
FIG. 4 illustrates thermal neutron density with respect to distance from source.

FIG. 4 illustrates thermal neutron density with respect to distance from source. Referring to FIG. 1, there are three zones: a short-spacing zone where the neutron density increases with porosity, a cross-over zone where TND is not sensitive to porosity, and a long-spacing zone where TND decreases as porosity increases. Since the neutron density and distance from the source in the long spacing region show an approximately linear relationship, the neutron porosity can be determined from the slope of these lines. The slope can be found from the ratio of count rates in two detectors placed at different distances (both in the long-spacing zone) from the source. This is typically the basis of modern compensated neutron instruments.

However, this type of measurement is affected by the absorption of thermal neutrons by elements in the formation other than the hydrogen in the pore-filling fluid. This is particularly problematic in unconventional reservoirs containing trace elements of materials which are significantly absorptive of thermal neutrons, referred to herein as a "dominant thermal neutron absorber." These dominant thermal neutron absorbers, such as, for example, boron and gadolinium, can cause significant problems with thermal neutron measurements, yielding inaccurate formation evaluation, when present in concentrations exceeding only a few parts per million. This is especially problematic in the case of porosity estimation.

Aspects of the present disclosure include a reliable correction method increasing accuracy in formation evaluation using compensated neutron tools. Aspects of the disclosure include novel techniques for correction of the compensated neutron response in the presence of dominant thermal neutron absorbers, which may be applied directly to information obtained from the conventional compensated neutron log.

In aspects of the disclosure, a joined processing method using multiple log responses, including pulsed neutron spectroscopy logs and conventional logging measurements such as compensated neutron and thermal neutron capture cross-section (SIGMA), may be implemented in the model to quantitatively obtain a "clean" neutron response by removing the excess thermal neutrons contributed by the dominant thermal neutron absorbers which are not included in the formation model.

Techniques of the Present Disclosure

The present disclosure includes methods, systems, and devices for correcting a compensated thermal neutron porosity measurement. Techniques described herein may be directed to estimating at least one correction factor by processing a log of compensated thermal neutron porosity measurements taken in a fluid-saturated rock matrix. The correction factor may be derived by first estimating a correlation function from compensated thermal neutron porosity measurements. The correction factor may be used to mitigate the effects of "excess" porosity in the porosity measurement. This "excess" porosity is the result of absorption of thermal neutrons by the dominant thermal neutron absorbers in the formation uncharacteristic to the formation's macroscopic conditions (e.g., lithology). Thus, the correlation function represents an estimation of a relation between excess porosity in the compensated thermal neutron porosity measurement and an excess in another measurement type. The correction factor may be applied to the whole formation, the whole logging section, or may be applied level by level. Thus, a plurality of correction factors may be estimated and applied to the corresponding measurements, with each correction factor of the plurality corresponding to a particular volume of the formation. The level may be determined prior to, during, or after the logging run. For example, the volume may correspond to prior estimations of lithology, porosity, or other characterizations of the greater formation, or may be selected post hoc in dependence upon changes in thermal neutron porosity measurements or other measurements.

Processing may include modeling each measurement of the compensated thermal neutron porosity measurements of the log as resulting from at least: i) a first contribution correlated to an absorbance of a first portion of neutrons produced by irradiation of the volume attributable to interactions in the volume indicative of pore space in the matrix, ii) a second contribution correlated to an absorbance of a second portion of the neutrons produced by the irradiation of the volume attributable to trace elements of at least one dominant neutron absorber in the formation; and iii) a third contribution correlated to an absorbance of a third portion of the neutrons produced by the irradiation of the volume attributable to dry minerals in the matrix other than dominant neutron absorbers. The interactions in the volume indicative of pore space in the matrix may predominantly comprise neutron absorption by hydrogen. The processing may include modeling the second contribution as excess porosity, including estimating the second contribution and determining the correction factor from the second contribution.

Estimating the correction factor may be carried out by jointly processing the log of compensated thermal neutron porosity measurements in combination with a second log of a location-dependent non-porosity measurement. The processing may include modeling the measurements of the second log as resulting from at least: i) a first contribution correlated to an absorbance of a first portion of neutrons produced by irradiation of the volume attributable to interactions in the volume indicative of pore space in the matrix, ii) a second contribution correlated to an absorbance of a second portion of the neutrons produced by the irradiation of the volume attributable to trace elements of at least one dominant neutron absorber in the formation, iii) a third contribution correlated to an absorbance of a third portion of the neutrons produced by the irradiation of the volume attributable to dry minerals in the matrix other than dominant neutron absorbers; and estimating the second contribution and determining the correction factor from the second contribution. The second log may be, for example, a log of thermal neutron capture cross section measurements.

Previous attempts at correction attempted to use physical properties of the formation, slowing-down length and diffusion length, to describe the compensated neutron response to porosity, salinity, and independent formation SIGMA changes. The rationale is that the slowing-down length Ls represents the behavior of epithermal neutron porosity devices, and the diffusion length Ld describes the appropriate length scale of the thermal diffusion phase. It can be thought of as the distance a thermal energy neutron travels between the point at which it became thermal until its final capture. The most accepted approach for forming a predictive model for compensated behavior has used the concept of migration length. The migration length Lm, is defined as the quadratic combination of the slowing down length Ls and the diffusion length Ld. Unfortunately, for formations with complex mineralogical compositions, such as shale gas reservoirs, it is difficult to know the exact amount of trace elements in advance. Thus, application of this model to remove the additional neutron readings resulting from the presence of thermal neutron absorbers is impractical.

Aspects of the present disclosure include the correction of compensated thermal neutron porosity using SIGMA logs. To the first order, once the log has been environmentally corrected, the compensated thermal neutron reading for a clean formation without influence of trace elements of dominant neutron absorbers can be characterized by a linear mixing law, referred to as theoretical compensated neutron $CN_{TH}$:

$$CN_{TH} = \Sigma V_{min,i} CN_{min,i} + \phi_t CN_{fld} \quad (1)$$

where $V_{min,i}$ is the dry mineral volume fraction of the $i^{th}$ mineral in a whole rock model, $CN_{min,i}$ is the compensated neutron measurement for the $i^{th}$ mineral (e.g., the 100 percent pure mineral standard response), $\phi_t$ is the formation total porosity, and $CN_{fld}$ is the apparent compensated neutron measurement from the fluids present in the formation (e.g., 100 percent pure fluid mixture response). The contribution from the trace elements of dominant neutron absorbers is added to this expression of the clean formation of into Eq. (1):

$$CN = \Sigma V_{min,i} CN_{min,i} + \phi_t CN_{fld} + CN_{excess} \quad (2).$$

where $CN_{excess}$ represents the compensated neutron response from the trace elements of dominant neutron absorbers. Thus, the correction factor may be estimated from $CN_{excess}$.

Similar equations can be applied to apportion the contributions of each component to a second measurement, such as, for example, the SIGMA measurement:

$$SIGMA_{TH} = \Sigma V_{min,i} SIGMA_{min,i} + \phi_t SIGMA_{fld} \quad (3)$$

$$SIGMA = \Sigma V_{min,i} SIGMA_{min,i} + \phi_t SIGMA_{fld} + SIGMA_{excess} \quad (4),$$

where $SIGMA_{min,i}$ is the SIGMA reading for the $i^{th}$ mineral (e.g., the 100 percent pure mineral standard response), $SIGMA_{fld}$ is the SIGMA apparent reading from the fluids present in the formation (e.g., 100 percent pure fluid mixture response), and $SIGMA_{excess}$ represents the SIGMA response from the trace elements of dominant neutron absorbers.

If the volume fractions of all minerals and porosity in the formation can be determined while all neutron and SIGMA parameters for them are known, the excess neutron term $CN_{excess}$ and excess SIGMA term $SIGMA_{excess}$ can be easily calculated using Eqs. (2) and (4), using mineral volume fractions and porosity estimated from pulsed neutron spectroscopy logs using, for example, stochastic methods (e.g., such as those embodied by the GliderMin software suite commercially available from Baker Hughes, a GE company, LLC or deterministic methods (e.g., from commercially available software such as ProLith).

Alternatively, estimating the contribution from the trace elements of dominant neutron absorbers may be carried out by performing an inversion using the results (measurements) of the first log and the second log. Such an inversion may be constrained with a priori information (e.g., previous logs) or optimized using various techniques. Performing the inversion may include determining a best fit using a least square error minimization.

Figure 5:
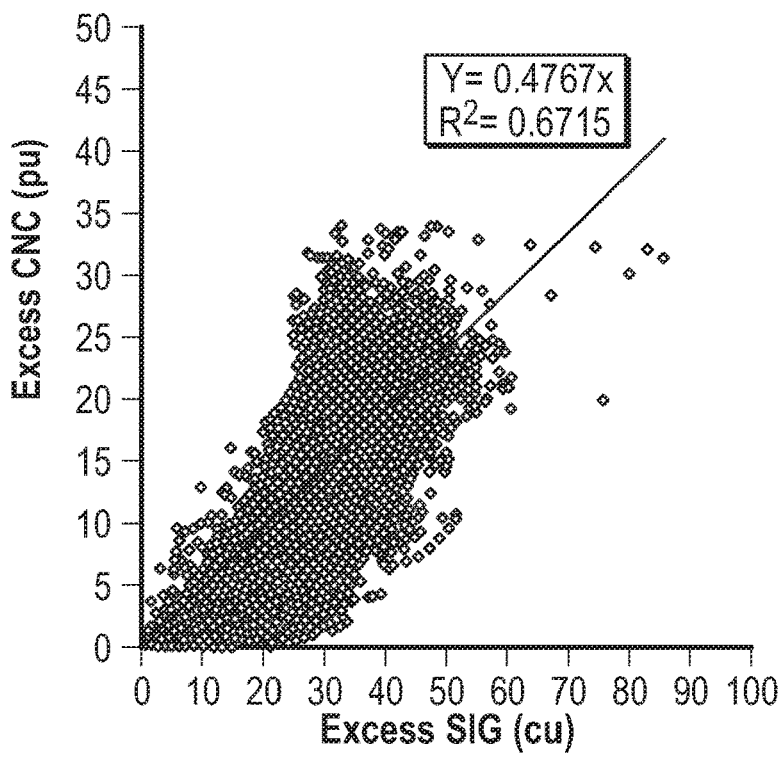
FIG. 5 is a graphical representation of a collection of data points from measurements illustrating $CN_{excess}$ with respect to $SIGMA_{excess}$.

FIG. 5 is a graphical representation of a collection of data points from measurements illustrating $CN_{excess}$ with respect to $SIGMA_{excess}$. FIG. 5 shows a direct correlation between the excess contributions. Interpolation of such results under various conditions or lithologies may result in determination of a relation between excess contributions of the compensated neutron and excess contributions of the second measurement type. In some instances, the excess contributions of the dominant neutron absorbers to the compensated neutron measurement may be expressed as a function of the excess contributions of the dominant neutron absorbers to the second measurement type, or correlation function. This function may be used to constrain an inversion, as described above. The function may be expressed as a function of SIGMA and $SIGMA_{excess}$:

$$CN_{excess} = f(SIGMA) * SIGMA_{excess}. \quad (5)$$

The exact nature of this function may vary with the particular application. In some cases, interpretations combining mineralogy-corrected porosity, grain density, and theoretical SIGMA and neutron responses from mineralogy from historical log examples show a simple yet effective correlation:

$$CN_{excess} = coefficient * SIGMA_{excess}. \quad (6)$$

The specific coefficient(s) of Eq. (6) vary from formation to formation but the value typically displays less than a 10 percent variance. Thus, standard values may be selected based on lithology, mineralogy, and other properties of the formation. The function may also be estimated for a particular formation or borehole. The function (or coefficient(s) of the function) may be determined using various techniques known in the art, and can be calculated based on local knowledge and core measurements, or can be estimated using multi-mineral analysis. The correlation may be linear or non-linear.

Comparing the results against core analysis data, experimental results provided much more accurate measurements. In one test, applying the correction model, the original processing results indicated much higher formation porosity with 20-60 percent overestimation compared with core measurements, due to trace elements in the formation. After applying the proposed correction, the adjusted porosity values were dramatically improved, matching well with core porosity measurements (within 5 percent).

Figure 6A:
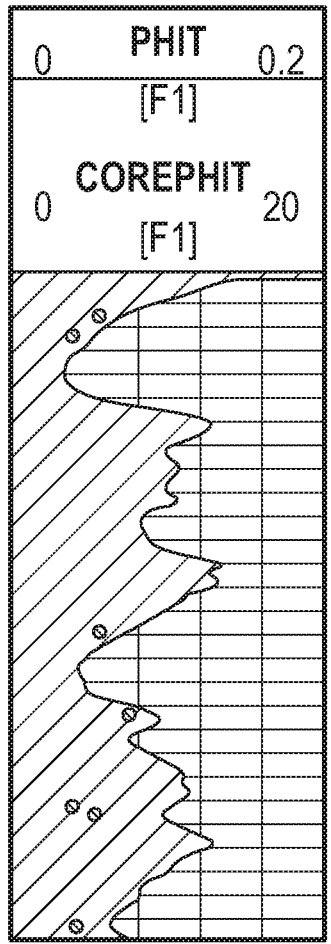
FIGS. 6A & 6B show an example of calculated total porosity for a shale gas well using a probabilistic program.
Figure 6B:
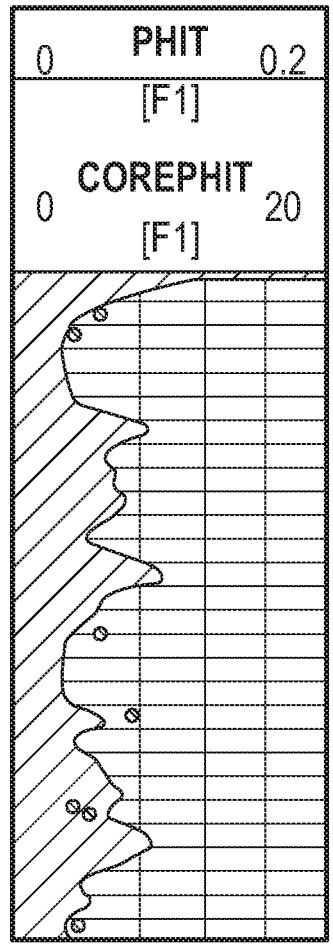

FIGS. 6A & 6B show an example of calculated total porosity for a shale gas well using a probabilistic program. Comparison of FIG. 6A, which includes a curve representing total porosity calculations before excess-neutron correction, and FIG. 6B, which includes a curve representing total porosity calculations after excess-neutron correction is illustrative. The dots in each figure represent core measurements. It should be noted in particular the significant correction applied in the lower part of the log. The total porosity results before applying excess-neutron correction are significantly higher than the core measurements due to the presence of the trace elements. After applying excess-neutron correction, the total porosity curve matches the core measurements very well, and thus the effectiveness of the proposed algorithm is apparent.

Figure 7A:
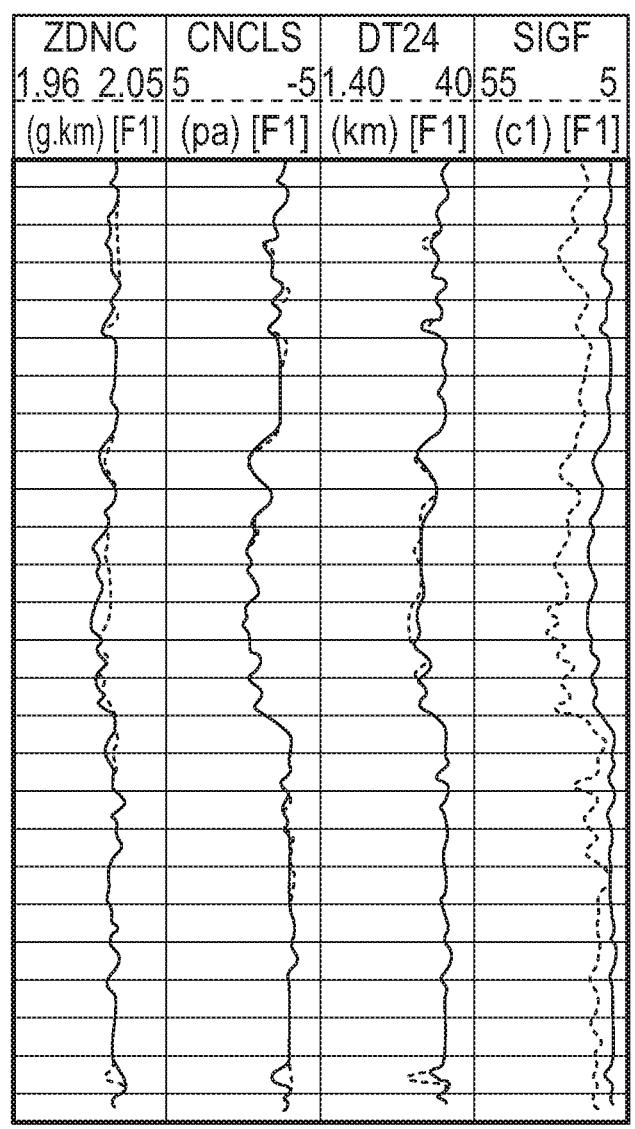
Figure 7C:
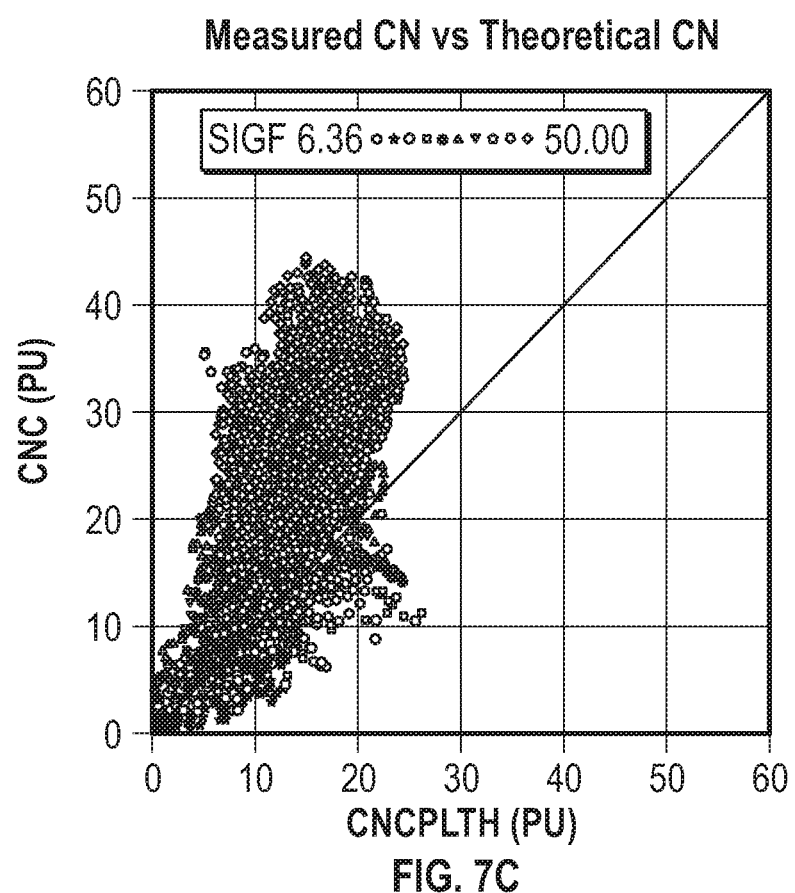
FIG. 7C shows measured experimental versus theoretical values for compensated neutron porosity.
Figure 7D:
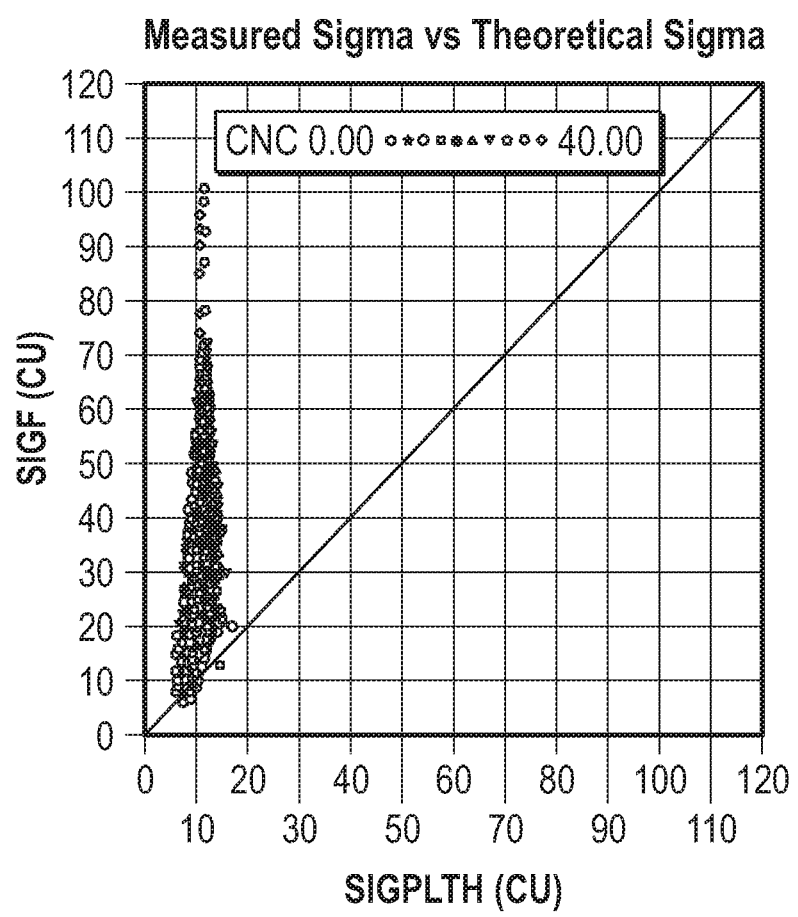
FIG. 7D shows measured experimental versus theoretical values for SIGMA.

FIGS. 7A & 7B show processing results before and after applying excess-neutron correction for a shale gas well, respectively. The logs of FIG. 7A show apparent mismatch for SIGMA and compensated neutron log measurements and the theoretical responses. This mismatch, caused by the existence of trace elements, could overestimate the porosity results in stochastic programs. The values of the theoretical response are the responses to components in the petrophysical model, from which the effects of excess sigma are absent. These responses may be considered clean in a theoretical sense. After applying the correction, the theoretical curves of FIG. 7B match with the measured logs. Curves 411 and 413 represent the excess responses for compensated neutron and SIGMA logs due to trace elements, respectively. FIGS. 7C & 7D show measured experimental versus theoretical values for compensated neutron porosity and SIGMA, respectively.

Figure 8:
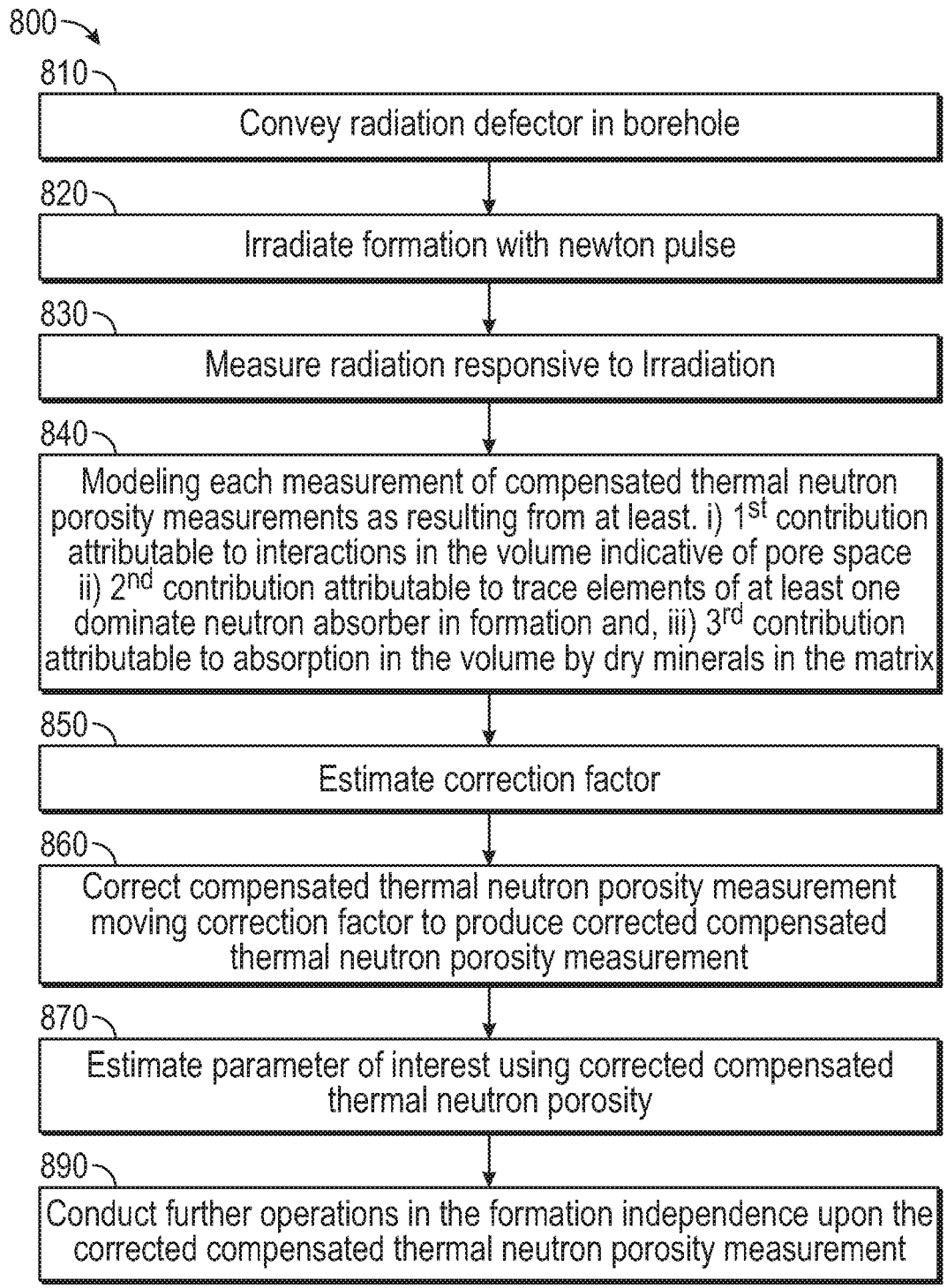
FIG. 8 illustrates methods in accordance with embodiments of the present disclosure.

FIG. 8 illustrates methods in accordance with embodiments of the present disclosure. Optional step 810 of method 800 comprises conveying a radiation detector downhole using a carrier. Step 820 comprises irradiating the earth formation with a neutron pulse produced by a pulsed neutron source disposed in the borehole to produce gamma-rays. Step 830 comprises measuring radiation responsive to the irradiation to generate compensated thermal neutron porosity measurements. Collectively, these measurements comprise a compensated thermal neutron porosity log. The log may comprise a varying location-dependent compensated thermal neutron porosity measurement.

Step 840 comprises modeling each measurement of the compensated thermal neutron porosity measurements of the log as resulting from at least: i) a first contribution correlated to an absorbance of a first portion of neutrons produced by irradiation of the volume attributable to interactions in the volume indicative of pore space in the matrix, ii) a second contribution correlated to an absorbance of a second portion of the neutrons produced by the irradiation of the volume attributable to trace elements of at least one dominant neutron absorber in the formation; and iii) a third contribution correlated to an absorbance of a third portion of the neutrons produced by the irradiation of the volume attributable to dry minerals in the matrix other than dominant neutron absorbers.

The interactions in the volume indicative of pore space in the matrix may predominantly comprise neutron absorption by hydrogen. The processing may include modeling the second contribution as excess porosity, including estimating the second contribution and determining the correction factor from the second contribution.

Step 850 comprises estimating the correction factor. Estimating the correction factor may be carried out by jointly processing the log of compensated thermal neutron porosity measurements in combination with a second log of a location-dependent non-porosity measurement. The processing may include modeling the measurements of the second log as resulting from at least: i) a first contribution correlated to an absorbance of a first portion of neutrons produced by irradiation of the volume attributable to interactions in the volume indicative of pore space in the matrix, ii) a second contribution correlated to an absorbance of a second portion of the neutrons produced by the irradiation of the volume attributable to trace elements of at least one dominant neutron absorber in the formation, iii) a third contribution correlated to an absorbance of a third portion of the neutrons produced by the irradiation of the volume attributable to dry minerals in the matrix other than dominant neutron absorbers; and estimating the second contribution and determining the correction factor from the second contribution. The second log may be a log of thermal neutron capture cross section measurements. Alternatively, estimating the second contribution of the first log may be carried out by performing an inversion using the results of the first log and the second log. Constraining the inversion may be carried out with the constraint that each second contribution of the first log is a function of the second contribution of a corresponding measurement of the second log.

Optional steps may include making at least one other radiation measurement with at least one of the detectors. The at least one other radiation measurement may measure radiation comprising gamma rays predominantly resulting from at least one of inelastic scattering and capture of neutrons. Each of the measurements and the other measurements may comprise a count having an associated relative energy channel. The calibration radiation spectrum may comprise an expression of gamma ray count rate with respect to relative energy channel for the measurements of radiation with the detector in the time interval. Each relative energy channel may be initially associated with or represented by a placeholder value, such as, for example, the energy value resulting from a previous calibration. Alternatively, the energy channel may be represented by a channel number or the like.

Step 860 comprises correcting a compensated thermal neutron porosity measurement using the correction factor to produce a corrected compensated thermal neutron porosity measurement. Optionally, step 870 of method 800 may include estimating a parameter of interest using the corrected compensated thermal neutron porosity. The corrected compensated thermal neutron porosity, the estimated parameter, and/or the correction factor may be stored as a record, transmitted uphole, and/or displayed to an operating engineer.

Optional step 880 comprises conducting further operations in the formation in dependence upon the corrected compensated thermal neutron porosity measurement. The further operations may comprise at least one of: i) geosteering; ii) drilling at least one borehole in the formation; iii) performing measurements on the formation; iv) estimating at least one parameter of interest of the formation; v) installing equipment in a borehole in the formation; vi) evaluating the formation; vii) optimizing development in the formation; viii) optimizing development in a formation related to the formation; ix) optimizing exploration in the formation; x) optimizing exploration in a formation related to the formation; xi) producing at least one hydrocarbon from the formation.

In some embodiments, estimation of the parameter of interest may involve applying a model. The model may include, but is not limited to, (i) a mathematical equation, (ii) an algorithm, (iii) an energy spectrum deconvolution technique, (iv) an energy spectrum stripping technique, (v) an energy spectrum window technique, (vi) a time spectrum deconvolution technique, (vii) a time spectrum window technique, or a combination thereof.

Figure 9:
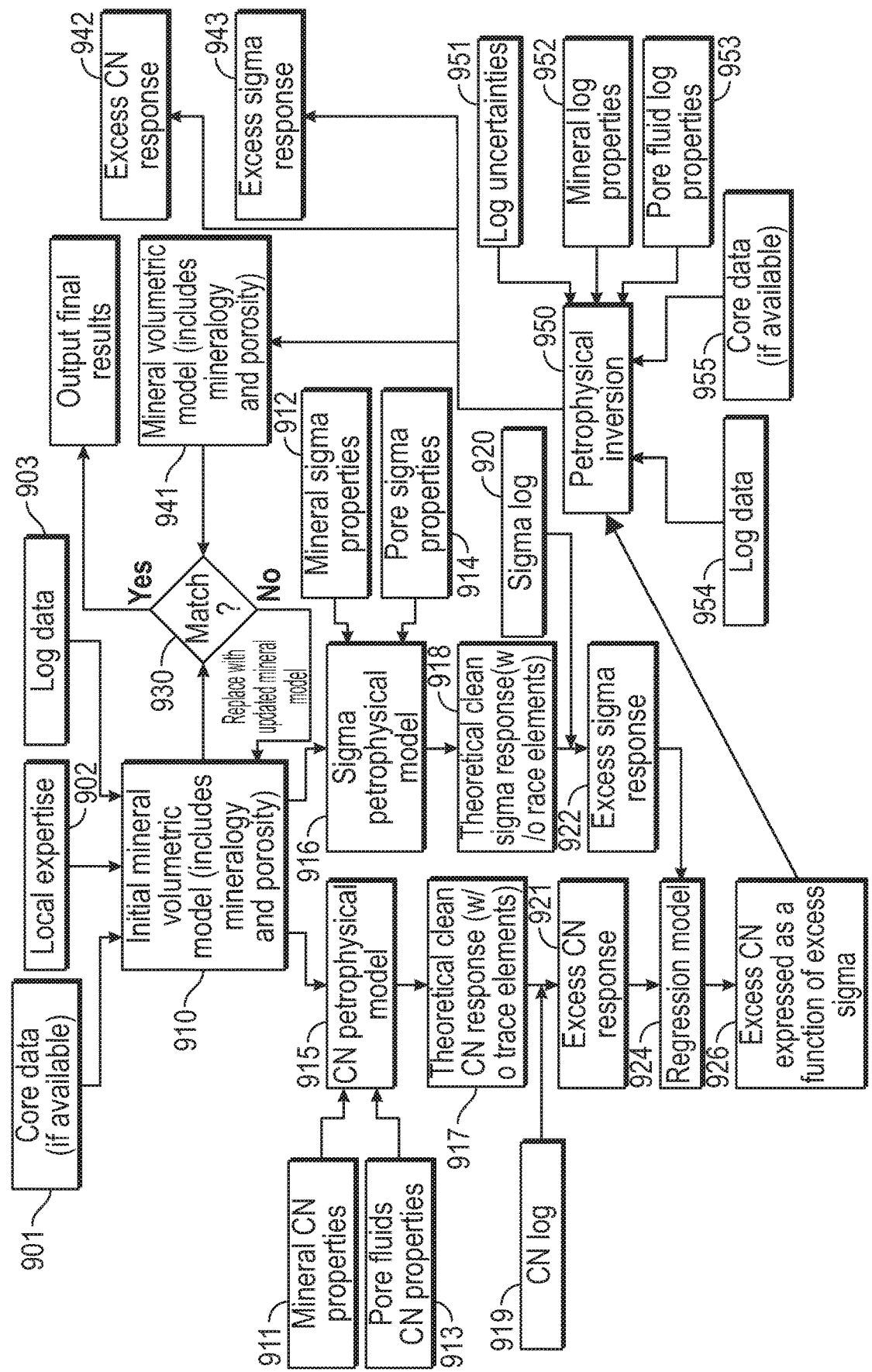
FIG. 9 shows a flow diagram in accordance with embodiments of the present disclosure.

FIG. 9 shows a flow diagram illustrating methods in accordance with embodiments of the present disclosure. Forward models are used to generate theoretical clean responses for both compensated neutron and a secondary log, such as SIGMA, from initial mineral volumetric model. Beginning at 910, an initial mineral volumetric model including, for example, mineralogy and porosity, may be estimated. Deterministic methods or probabilistic methods may be employed to derive the initial mineral volumetric model 910, using any or all of log data 903 indicative of elemental and mineralogical composition (e.g., gamma ray spectra), core data 901, and a priori knowledge 902 (e.g., ground truth, local expertise, etc.). Alternatively, an initial stochastic model may be utilized.

The initial mineral volumetric model 910 is then used to build a compensated formation model, such as a compensated neutron petrophysical model 915 and a SIGMA petrophysical model 916. The compensated neutron (CN) petrophysical model 915, such as one reflecting Eq. (1), is built using mineral CN properties 911 and pore fluid CN properties 913. The SIGMA petrophysical model 916, such as one reflecting Eq. (3), is built using mineral SIGMA properties 912 and pore fluid SIGMA properties 914. A theoretical clean CN response 917—that is, one that is free off contributions from trace elements of dominant absorbers— is calculated from the model 915. A theoretical clean SIGMA response 918 (also free off contributions from trace elements of dominant absorbers) is calculated from the model 916.

The theoretical clean CN response 917 and the theoretical clean SIGMA response 918 are compared with the compensated neutron log 919 and SIGMA log 920, respectively, in order to estimate excess CN response 92 land excess SIGMA response 922. As one example, Eq. (2) and Eq. (4), may be used to estimate the excess CN response 921 and excess SIGMA response 922. Regression model 924 is utilized upon the data points of excess CN response 921 and excess SIGMA response 922 over several measurements (e.g., at several measurement depths) to determine a regression function (correlation function 926), which expresses excess CN as a function of excess sigma. This expression allows conversion of a pair of variables corresponding to the two logs to a single variable for an inversion. The regression function may be linear or non-linear.

Module 950 carries out a petrophysical inversion constrained by the correlation function 926. Module 950 may also use any or all of log uncertainties 951, mineral log properties 952, pore fluid log properties 953, core data 955, and log data 954 in the inversion.

The inversion may produce a mineral volumetric model 941 (e.g., including mineralogy and porosity), excess CN response 942, and excess sigma response 943. This inversion may be done once, or it may be done iteratively by comparing the model 941 with the model previously used as the initial model 910 in module 930. If the two models do not substantially match (N), the initial model is updated with model 941 (e.g., may be replaced with model 941). When the models substantially match, the current version of model 941 may be output as the final result. The models substantially match when they differ by less than a threshold metric, such as, for example, a cost function (e.g., least squares optimization), percentage difference (e.g., less than 1 percent difference, less than 0.1 percent difference, and so on).

Returning to FIG. 1A, certain embodiments of the present disclosure may be implemented with a hardware environment 80 that includes an information processor 81, a information storage medium 83, an input device 85, processor memory 87, and may include peripheral information storage medium 89. The hardware environment 80 may be in the well, at the rig, or at a remote location. Moreover, the several components of the hardware environment may be distributed among those locations. The input device 85 may be any information reader or user input device, such as data card reader, keyboard, USB port, etc. The information storage medium 83 stores information provided by the detectors. Information storage medium 83 may be any standard computer information storage device, such as a ROM, USB drive, memory stick, hard disk, removable RAM, EPROMs, EAROMs, EEPROM, flash memories, and optical disks or other commonly used memory storage system known to one of ordinary skill in the art including Internet based storage. Information storage medium 83 stores a program that when executed causes information processor 81 to execute the disclosed method. Information storage medium 83 may also store the formation information provided by the user, or the formation information may be stored in a peripheral information storage medium 89, which may be any standard computer information storage device, such as a USB drive, memory stick, hard disk, removable RAM, or other commonly used memory storage system known to one of ordinary skill in the art including Internet based storage. Information processor 81 may be any form of computer or mathematical processing hardware, including Internet based hardware. When the program is loaded from information storage medium 83 into processor memory 87 (e.g., computer RAM), the program, when executed, causes information processor 81 to retrieve detector information from either information storage medium 83 or peripheral information storage medium 89 and process the information to estimate a parameter of interest. Information processor 81 may be located on the surface or downhole.

Estimated corrected compensated thermal neutron porosity measurement values and/or models of the formation (or portions thereof) may be stored (recorded) as information or visually depicted on a display. The visual depiction may include a two-dimensional (2D) or three dimensional (3D) graphical depiction of corrected compensated thermal neutron porosity measurement values (although one-dimensional (1D) depictions may also be displayed in some applications). The corrected compensated thermal neutron porosity measurement values or model may be transmitted before or after storage or display, such as, for example, being transmitted uphole (i.e., to the surface or to modules closer to the surface). For example, information may be transmitted to other downhole components, or to the surface for storage, display, or further processing. Aspects of the present disclosure relate to modeling a volume of an earth formation using the estimated corrected compensated thermal neutron porosity measurement values, such as, for example, by associating corrected compensated thermal neutron porosity measurement values with portions of the volume of interest to which they correspond, or by representing a boundary between areas of representative or statistically similar values along with the formation in a global coordinate system. Aspects include maintaining a model comprising a representation of the earth formation stored as information including a representation of corrected compensated thermal neutron porosity measurement values with respect to location, either as absolute values or variances thereof. The model of the earth formation generated and maintained in aspects of the disclosure may be implemented as a representation of the earth formation stored as information, including a graphic representation of corrected compensated thermal neutron porosity measurement values or variances in corrected compensated thermal neutron porosity measurements or other parameters of interest (including, for example, parameters derivable using corrected compensated thermal neutron porosity measurements) with respect to location, e.g., in 1D, 2D, or 3D. In one example, a model of the earth formation may be maintained in a database. Modeling the earth formation may comprise associating a portion of the formation proximate the borehole with the corrected compensated thermal neutron porosity measurement as estimated herein, to generate or update the model. The information (e.g., data) may also be transmitted, stored on a non-transitory machine-readable medium, and/or rendered (e.g., visually depicted) on a display. Any of rendering the models, the values, or information representing the same may be referred to herein as "displaying the corrected compensated thermal neutron porosity measurement on a display."

The processing of the measurements by a processor may occur at the tool, the surface, or at a remote location. The data acquisition may be controlled at least in part by the electronics. Implicit in the control and processing of the data is the use of a computer program on a suitable non-transitory machine readable medium that enables the processors to perform the control and processing. The non-transitory machine readable medium may include ROMs, EPROMs, EEPROMs, flash memories and optical disks. The term processor is intended to include devices such as a field programmable gate array (FPGA).

The term "processor" or "information processing device" herein includes, but is not limited to, any device that transmits, receives, manipulates, converts, calculates, modulates, transposes, carries, stores or otherwise utilizes information. An information processing device may include a microprocessor, resident memory, and peripherals for executing programmed instructions. The processor may execute instructions stored in computer memory accessible to the processor, or may employ logic implemented as field-programmable gate arrays ('FPGAs'), application-specific integrated circuits ('ASICs'), other combinatorial or sequential logic hardware, and so on. Thus, a processor may be configured to perform one or more methods as described herein, and configuration of the processor may include operative connection with resident memory and peripherals for executing programmed instructions.

In some embodiments, estimation of the parameter of interest (water saturation) may involve applying a model, as described herein above. The model may include, but is not limited to, (i) a mathematical equation, (ii) an algorithm, (iii) a database of associated parameters, (iv) a rule set, (v) a heuristic, (vi) a function, and (vii) other relational techniques, or a combination thereof.

Control of components of apparatus and systems described herein may be carried out using one or more models as described above. For example, at least one processor may be configured to modify operations i) autonomously upon triggering conditions, ii) in response to operator commands, or iii) combinations of these. Such modifications may include changing drilling parameters, steering the drillbit (e.g., geosteering), changing a mud program, optimizing measurements, and so on. Control of these devices, and of the various processes of the system generally, may be carried out in a completely automated fashion or through interaction with personnel via notifications, graphical representations, user interfaces and the like. Reference information accessible to the processor may also be used.

Formation lithology may include formation mineral type, porosity, and fluid in the pore space. Mineralogy may be defined as the chemical composition and structure of minerals in the formation. Herein, "information" may include raw data, processed data, analog signals, and digital signals. The term "conveyance device" or "carrier" as used above means any device, device component, combination of devices, media and/or member that may be used to convey, house, support or otherwise facilitate the use of another device, device component, combination of devices, media and/or member. Exemplary non-limiting conveyance devices (carriers) include drill strings of the coiled tube type, of the jointed pipe type and any combination or portion thereof. Other conveyance device examples include casing pipes, wirelines, wire line sondes, slickline sondes, drop shots, downhole subs, BHA's, drill string inserts, modules, internal housings and substrate portions thereof, self-propelled tractors. As used above, the term "sub" refers to any structure that is configured to partially enclose, completely enclose, house, or support a device. The term "information" as used above includes any form of information (Analog, digital, EM, printed, etc.). The term "information processing device" herein includes, but is not limited to, any device that transmits, receives, manipulates, converts, calculates, modulates, transposes, carries, stores or otherwise utilizes information. An information processing device may include a microprocessor, resident memory, and peripherals for executing programmed instructions. The "correction factor" may be applied in additive (or subtractive) or multiplicative fashion to the radiation information including measurements and may be implemented as a function. The term "dominant thermal neutron absorber" refers to elements having a significant neutron capture cross section, e.g., sufficient to distort a compensated thermal neutron porosity measurement beyond normal use. A significant neutron capture cross section comprises more than 500 barns. Typical dominant thermal neutron absorbers may have a cross section of more than 1000 barns.

While the foregoing disclosure is directed to the one mode embodiments of the disclosure, various modifications will be apparent to those skilled in the art. It is intended that all variations be embraced by the foregoing disclosure.

What is claimed is:

1. A method for estimating at least one property of a volume of interest of an earth formation from a compensated thermal neutron porosity measurement, the volume of interest surrounding a borehole intersecting the earth formation, the method comprising:

estimating a correction factor by jointly processing a log of compensated thermal neutron porosity measurements taken in a fluid-saturated rock matrix in combination with a second log of a location-dependent non-porosity measurement, the processing comprising:

modeling each measurement of the compensated thermal neutron porosity measurements of the log as resulting from at least:

i) a first contribution correlated to an absorbance of a first portion of neutrons produced by irradiation of the volume, the absorbance of the first portion attributable to interactions in the volume indicative of pore space in the matrix, and ii) a second contribution correlated to an absorbance of a second portion of the neutrons produced by the irradiation of the volume, the absorbance of the second portion attributable to trace elements of at least one dominant neutron absorber in the formation, each of the at least one dominant neutron absorber having a neutron capture cross section of more than 500 barns, iii) a third contribution correlated to an absorbance of a third portion of the neutrons produced by the irradiation of the volume, the absorbance of the third portion attributable to dry minerals in the matrix other than dominant neutron absorbers;

estimating the second contribution and determining the correction factor from the second contribution; and correcting a compensated thermal neutron porosity measurement using the correction factor to produce a corrected compensated thermal neutron porosity measurement.

2. The method of claim 1, wherein the log of compensated thermal neutron porosity measurements comprises a varying location-dependent compensated thermal neutron porosity measurement.

3. The method of claim 1, wherein the interactions in the volume indicative of pore space in the matrix predominantly comprise neutron absorption by hydrogen.

4. The method of claim 1, wherein the parameter of interest is corrected compensated thermal neutron porosity.

5. The method of claim 1, wherein the processing comprises:

modeling the measurements of the second log as resulting from at least:

i) a first contribution correlated to an absorbance of a first portion of neutrons produced by irradiation of the volume attributable to interactions in the volume indicative of pore space in the matrix, ii) a second contribution correlated to an absorbance of a second portion of the neutrons produced by the irradiation of the volume attributable to trace elements of at least one dominant neutron absorber in the formation, iii) a third contribution correlated to an absorbance of a third portion of the neutrons produced by the irradiation of the volume attributable to dry minerals in the matrix other than dominant neutron absorbers; and estimating the second contribution of the first log and determining the correction factor from the second contribution.

6. The method of claim 5, wherein the second log is a log of thermal neutron capture cross section measurements.

7. The method of claim 5, comprising estimating the second contribution of the first log by performing an inversion using the results of the first log and the second log.

8. The method of claim 7, comprising:
constraining the inversion with the constraint that each second contribution of the first log is a function of the second contribution of a corresponding measurement of the second log.

9. The method of claim 8, comprising:
constraining the inversion with the constraint that each second contribution of the first log is a function of both the corresponding measurement and the second contribution of the corresponding measurement of the second log.

10. The method of claim 5, comprising:
estimating a correlation function defining a second contribution of a measurement of the first log as a function of at least one of: i) a corresponding measurement of the second log, and ii) a second contribution of the corresponding measurement of the second log.

11. The method of claim 7, wherein performing the inversion comprises determining a best fit using a least square error.

12. The method of claim 5, comprising generating a simulated theoretical clean compensated neutron response and a simulated theoretical clean compensated neutron response;

comparing the simulated theoretical clean compensated neutron response with the log of compensated thermal neutron porosity measurements to estimate the second contribution of the log of compensated thermal neutron porosity measurements; and comparing the simulated theoretical clean compensated neutron response with the measurements of the second log to estimate the second contribution of the second log.

13. The method of claim 1, further comprising determining the first contribution as a sum of respective contributions from volume fractions of a plurality of candidate minerals.

14. The method of claim 1, comprising conducting further operations in the formation in dependence upon the corrected compensated thermal neutron porosity measurement.

15. The method of claim 12, wherein the further operations comprise at least one of: i) geosteering; ii) drilling at least one borehole in the formation; iii) performing measurements on the formation; iv) estimating at least one parameter of interest of the formation; v) installing equipment in a borehole in the formation; vi) evaluating the formation; vii) optimizing development in the formation; viii) optimizing development in a formation related to the formation; ix) optimizing exploration in the formation; x) optimizing exploration in a formation related to the formation; xi) producing at least one hydrocarbon from the formation.

16. An apparatus for estimating at least one property of a volume of interest of an earth formation from a compensated thermal neutron porosity measurement, the volume of interest surrounding a borehole intersecting the earth formation, the method comprising:

a carrier having a tool disposed thereon and configured for conveyance in a borehole, the tool configured to make radiation-based measurements including compensated thermal neutron porosity measurements;

at least one information processing device configured to perform:

generating a log of compensated thermal neutron porosity measurements taken in the fluid-saturated rock matrix using the tool;

estimating a correction factor by jointly processing the log of compensated thermal neutron porosity measurements in combination with a second log of a location-dependent non-porosity measurement, the processing comprising:

modeling each measurement of the compensated thermal neutron porosity measurements of the log as resulting from at least:

i) a first contribution correlated to an absorbance of a first portion of neutrons produced by irradiation of the volume, the absorbance of the first portion attributable to interactions in the volume indicative of pore space in the matrix, and ii) a second contribution correlated to an absorbance of a second portion of the neutrons produced by the irradiation of the volume, the absorbance of the second portion attributable to trace elements of at least one dominant neutron absorber in the formation, each of the at least one dominant neutron absorber having a neutron capture cross section of more than 500 barns, iii) a third contribution correlated to an absorbance of a third portion of the neutrons produced by the irradiation of the volume, the absorbance of the third portion attributable to dry minerals in the matrix other than dominant neutron absorbers;

estimating the second contribution and determining the correction factor from the second contribution; and correcting a compensated thermal neutron porosity measurement using the correction factor to produce a corrected compensated thermal neutron porosity measurement.

* * * * *